United States Patent [19]
Griffin

[11] Patent Number: 5,909,831
[45] Date of Patent: Jun. 8, 1999

[54] SOCK AND SUPPORT HOSE INSTALLER DEVICE

[76] Inventor: Bernard L. Griffin, 5212 Millwood Rd., Montgomery, Ala. 36109

[21] Appl. No.: 09/109,394

[22] Filed: Jul. 2, 1998

Related U.S. Application Data

[60] Provisional application No. 60/075,486, Feb. 23, 1998.
[51] Int. Cl.⁶ .................................................. A47G 25/80
[52] U.S. Cl. ........................................... 223/112; 223/111
[58] Field of Search ................................... 223/111, 112, 223/113, 118, 114

[56] References Cited

U.S. PATENT DOCUMENTS

| | | |
|---|---|---|
| 4,066,194 | 1/1978 | Leland . |
| 4,284,216 | 8/1981 | Leland . |
| 4,651,909 | 3/1987 | Banting . |
| 4,943,097 | 7/1990 | Sanger . |
| 5,050,784 | 9/1991 | Turner ...................................... 223/114 |
| 5,249,720 | 10/1993 | White . |
| 5,632,424 | 5/1997 | Maier et al. . |
| 5,636,774 | 6/1997 | Moscato . |
| 5,687,889 | 11/1997 | Liden ...................................... 223/111 |
| 5,741,569 | 4/1998 | Votino et al. ............................ 223/112 |

*Primary Examiner*—Bibhu Mohanty
*Attorney, Agent, or Firm*—Tipton L. Randall

[57] ABSTRACT

The invention is a manually operable device for applying foot coverings including socks, support hose and the like. The device is made of an elongated U-shaped member of flexible material with a horizontal bottom and generally vertical sides. The side portions are adapted to flex toward each other when inserting the toe end into a foot covering and have a concave area for receiving and reversibly maintaining a foot covering when it is inserted over the toe ends. A strap is connected to the U-shaped member at the heel end. The strap is then used to draw the U-shaped member up the foot and leg and out of the open end of the foot covering, thereby positioning the foot covering on the foot and leg of the user.

7 Claims, 6 Drawing Sheets

1

SOCK AND SUPPORT HOSE INSTALLER DEVICE

This application claims the benefit of provisional application 60/075,486 filed Feb. 23, 1998.

FIELD OF THE INVENTION

The present invention relates to devices used to install foot coverings such as socks or support hose and, more particularly, to those devices which enable a person who is not otherwise able to put on foot coverings by themselves to don their socks without the assistance of another person.

BACKGROUND OF THE INVENTION

A large number of devices have been developed for the purpose of assisting with the donning of foot coverings. These devices are intended to help those who are injured, disabled or prevented for some reason from putting on their socks unassisted.

Sanger, in U.S. Pat. No. 4,943,097, describes a stocking installer with a solid handle affixed to the rear of the device.

White, in U.S. Pat. No. 5,249,720, discloses a hand operated spreader device for application of elastic stockings.

In U.S. Pat. No. 5,636,774 Moscato shows a flexible stocking spreader device powered by an electric motor.

Leland, in U.S. Pat. Nos. 4,066,194 and 4,284,216, discloses a device for assisting in the donning of a sock or like foot covering. The device is comprised of a wire like handle connected to a pair of sock expanding and holding members. The device is inserted in the sock and the sock expanding and holding members are spread using the handle to engage the sock. The handle is then used to install the sock over the foot. A similar wire frame device for installing stockings is described by Maier et al. In U.S. Pat. No. 5,632,424.

Liden, in U.S. Pat. No. 5,687,889, discloses a manually operable device to help those who cannot bend at the back, waist or knees don socks, shoes and pants. The device includes a handle and a plastic shovel used to apply socks. Use of the device requires the foot to be raised off the floor and inserted in the shovel while the device is held in place above the floor. This requires a certain amount of balance and dexterity.

Banting, in U.S. Pat. No. 4,651,909, discloses a manually operable device for applying socks or the like made of a flexible sheet material. The device is comprised of a flexible sheet material with two diverging edge formations on the toe portion and a flexible hinge segment between the toe and heel portions. The device is inserted in a sock and a thread is used to pull the device over the foot to install the sock.

Many of the prior art devices are somewhat complicated to manufacture and to use. None fully disclose all of the features and advantages of the present invention, which include extremely simple construction and the ability to place the installer flat on the floor for insertion of the user's foot. The user can then pause with the foot and installer resting on the floor for as long as desired before proceeding to pull the sock over the foot and up the leg. This allows those individuals with problems balancing to easily use the present invention and is a significant improvement over the prior art.

A further advantage of the present invention is the ease with which it is able to comfortably rotate around the user's heel while carrying the foot covering. Another advantage of the present invention is its ability to remain attached to the foot covering after the open end of the foot covering has been installed over the heel, thus enabling it to draw the foot covering up the leg of the user. A still further advantage of the present invention is the ease with which it is removed from the foot covering without the actuation of any controls or fasteners after the foot covering is in place on the users leg and foot.

SUMMARY OF THE INVENTION

The invention is a manually operable device for applying foot coverings including socks, support hose and the like. The device is made of an elongated U-shaped unitary member of flexible material with a horizontal bottom portion and generally vertical side portions. The U-shaped member has toe and heel ends. The side portions at the toe end extend beyond the toe end bottom portion and terminate in spade shaped ends adapted to flex toward each other when inserting the toe end into a foot covering. The side portions each have a concave area at about the midpoint for receiving and reversibly maintaining a foot covering when it is inserted over the toe ends. A strap is connected to the U-shaped member at the heel end.

The user inserts the spade shaped toe ends into the open end of a foot covering, positions a majority of the foot covering about the U-shaped member's concave side areas, and inserts a foot into the U-shaped member from the heel end. The strap attached to the heal end is then used to draw the U-shaped member up the foot and leg and out of the open end of the foot covering, thereby positioning the foot covering on the users foot and leg.

Also disclosed is a method of using the manually operable device for applying foot coverings, as well as method of making the device of the present invention.

The invention, together with further advantages and features thereof, may best be understood by reference to the following description, taken in connection with the accompanying drawings, in the figures of which like reference numerals identify like elements.

BRIEF DESCRIPTION OF THE DRAWINGS

Reference is next made to a brief description of the drawings, which are intended to illustrate the preferred embodiment of the sock and support hose installer of the present invention with respect to the manner of making and using the same in its presently understood best mode. The drawings and the detailed description which follow are intended to be merely illustrative and not otherwise limiting of the scope of the invention as set forth in the appended claims.

DESCRIPTION OF THE PREFERRED EMBODIMENT

Figure 1:
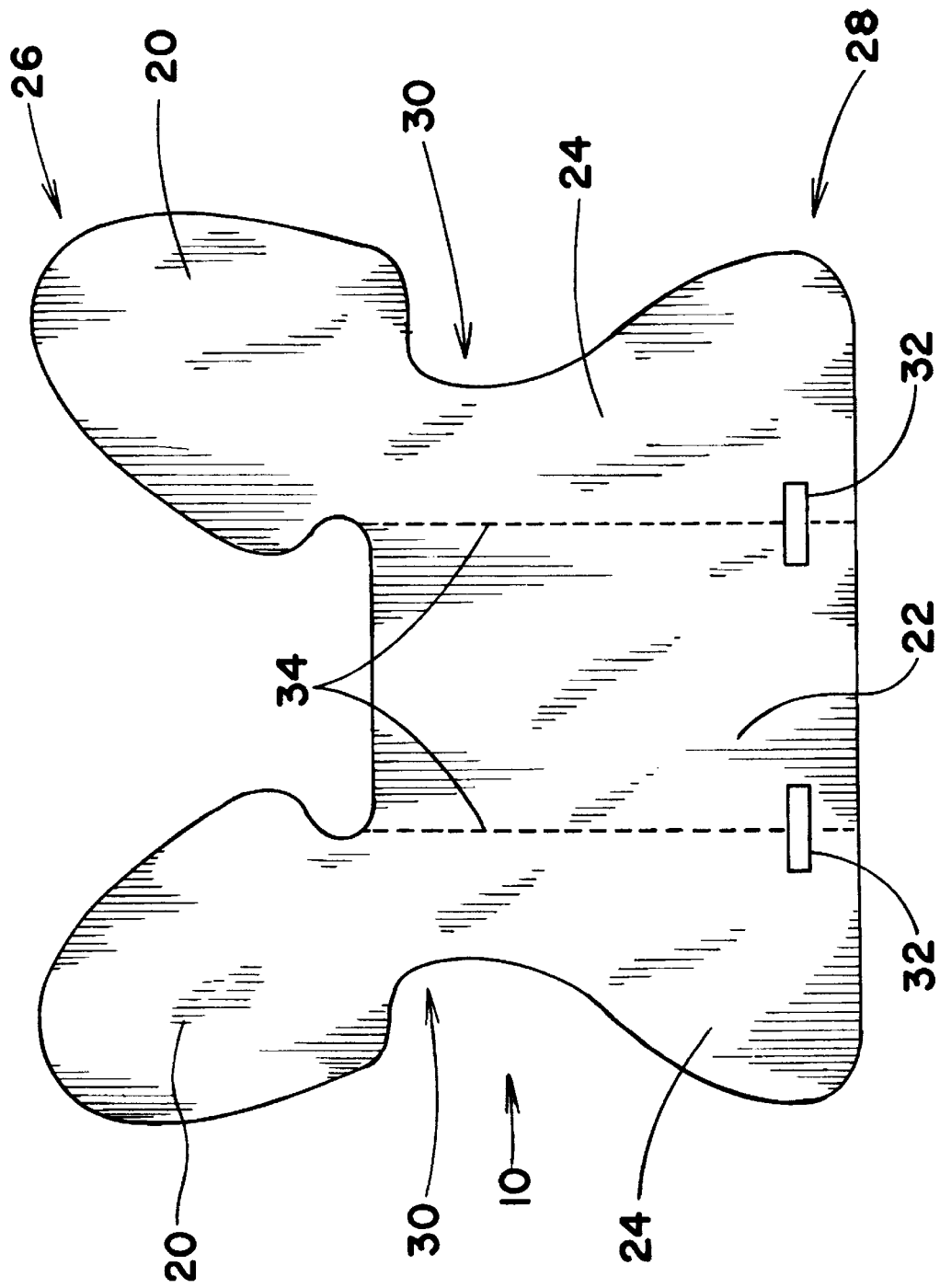
FIG. 1 is a top view of the flexible member of the sock and support hose installer of the present invention, as it would appear when cut from a sheet of material.
Figure 2:
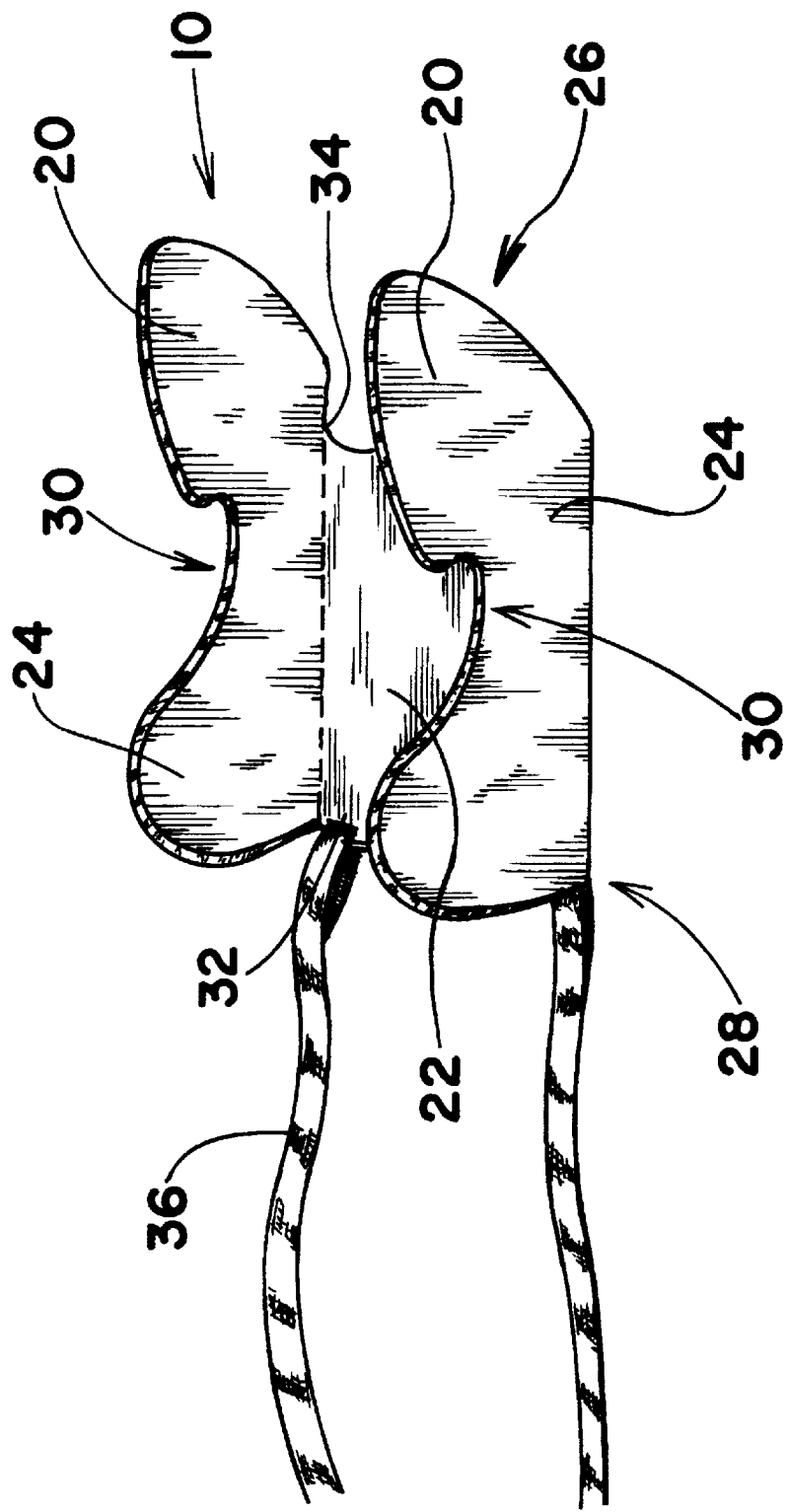
FIG. 2 is a perspective view of the sock and support hose installer after it has been formed.

Nomenclature:
- 10 U-Shaped Member
- 20 Spade Shaped End
- 22 Bottom Portion
- 24 Vertical Side Portion
- 26 Toe End of Member
- 28 Heel End of Member
- 30 Concave Side Portion
- 32 Strap Mounting Slot
- 34 Bend Line
- 36 Strap Means
- 38 Foot Covering
- 40 Opening of Foot Covering
- 42 Foot of User
- 44 Leg of User Construction:

The invention is a manually operable device for applying foot coverings including socks, support hose and the like. FIG. 1 shows a top view of the body 10 of the sock and support hose installer as it would appear when cut from a flexible sheet of suitable material. The material may be a synthetic polymeric material, such as a thermoplastic, or a flexible metal, such as sheet aluminum. The material is then formed, in the case of a sheet of thermoplastic material, by heating, while the cut sheet is pressed between form blocks into an elongated U-shaped member 10 resulting in the shape shown in FIG. 2.

The elongated U-shaped member 10 thus produced has a horizontal bottom 22 and two generally vertical sides 24. The sides 24 at the toe end 26 extend beyond the bottom 22 and terminate in spade shaped ends 20 adapted to flex toward each other when inserting the toe end 26 into a foot covering 38, shown in FIG. 3. Returning to FIG. 2, the strap 36 is connected to the U-shaped member 10 at the heel end 28 using, for example, the two slots 32 in the heel end 28. The sides 24 each have a concave area 30 at about the midpoint of the U-shaped member 10 for receiving and reversibly maintaining a foot covering 38 with an open end 40 which is inserted over the spade shaped ends 20 as shown in FIG. 3.

Figure 3:
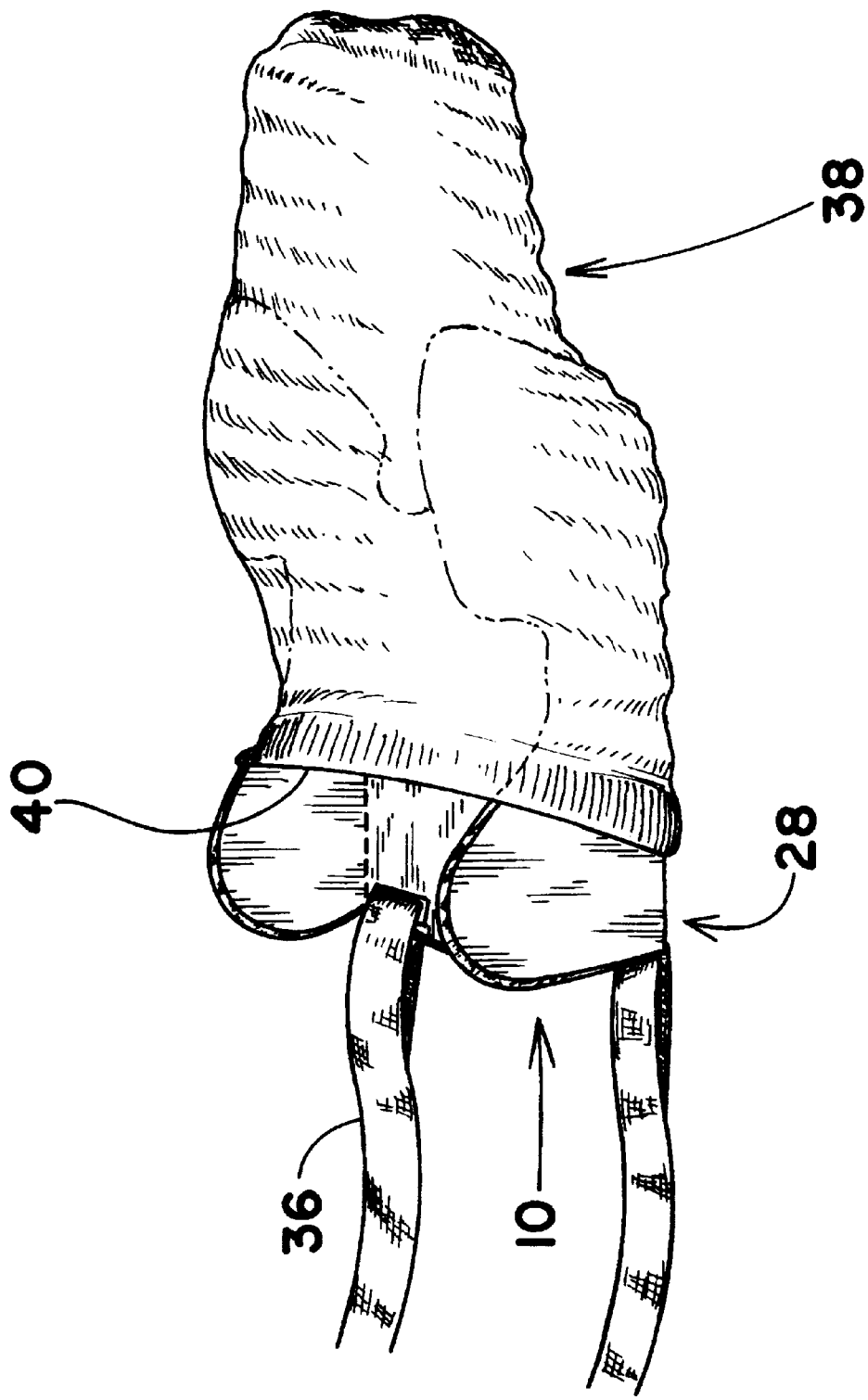
FIG. 3 is a perspective view showing the sock and support hose installer inserted into the open end of a sock.
Figure 4:
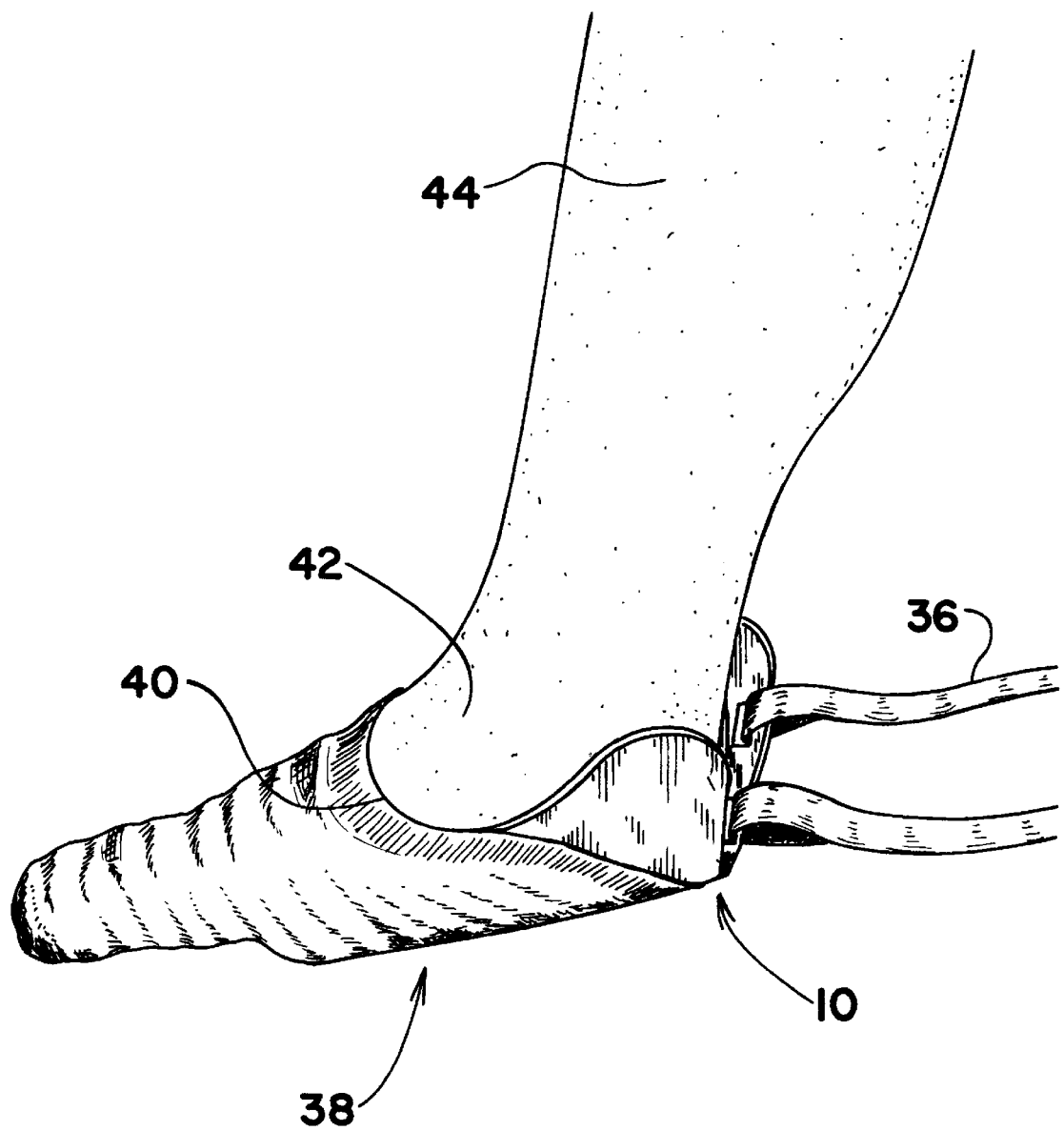
FIG. 4 is a perspective view of the sock and support hose installer showing the sock being drawn over the heel of the user.
Figure 5:
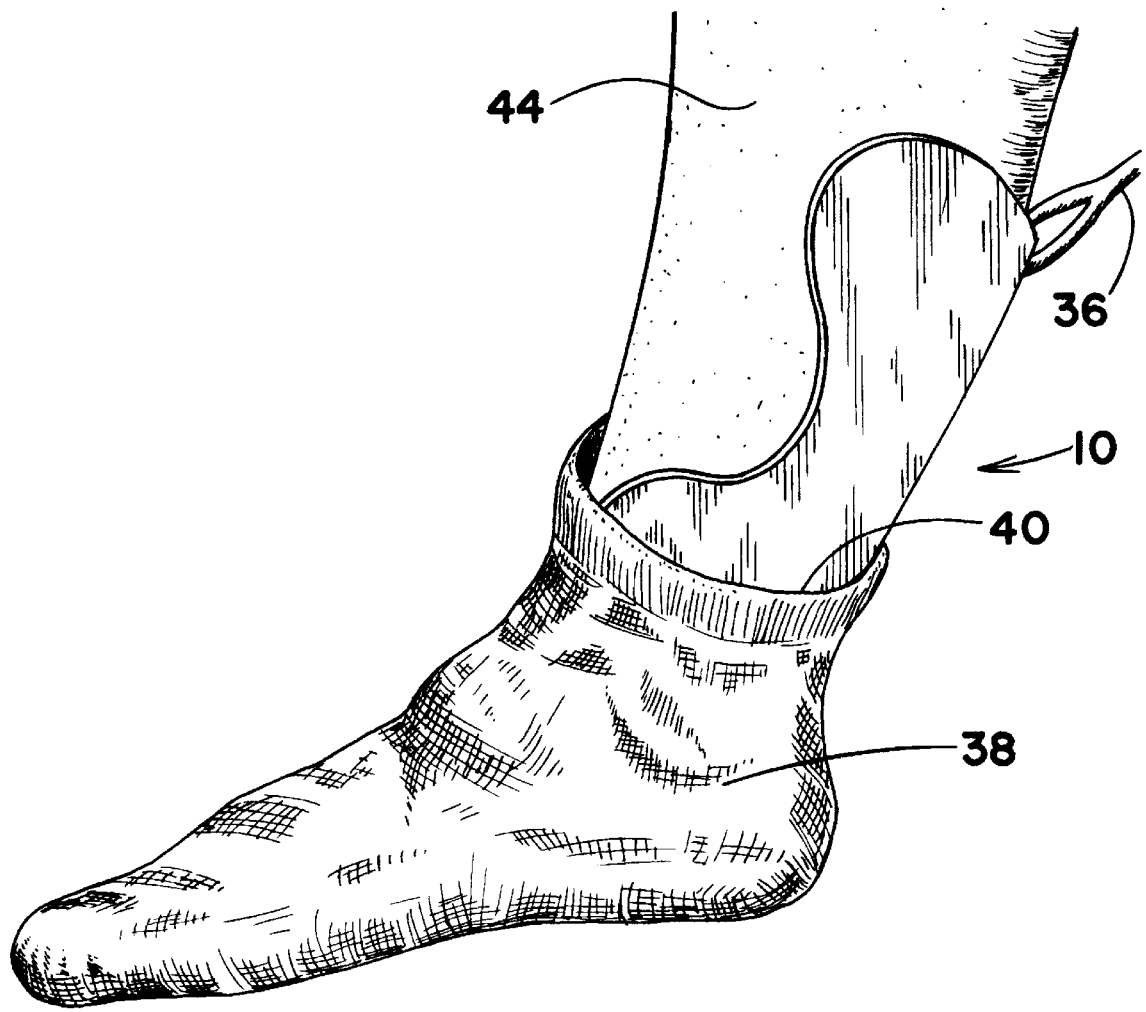
FIG. 5 is a perspective view showing the sock and support hose installer being removed from the sock on the leg of the user.

The user inserts the spade shaped toe ends 20 into the open end 40 of a foot covering 38 and positions a majority of the foot covering 38 about the concave areas 30 of the U-shaped member 10 as shown in FIG. 3. The user then inserts a foot 42 into the U-shaped member 10 from the heel end 28 as shown in FIG. 4. Both the foot 42 and the U-shaped member 10 can rest comfortably on the floor at this point for as long as desired. When the user is ready, the strap 36, attached to the heal end 28, is used to draw the U-shaped member 10 up the foot 42 and leg 44 and out of the open end 40 of the foot covering 38, thereby positioning the foot covering 38 on the foot 42 and leg 44 of the user as shown in FIG. 5.

An important advantage of the of the present invention is that the device 10 can be inserted into a sock 38 and then placed on the floor for easy insertion of the foot 42 with the user in either a standing or sitting position. There are no controls to be operated and the user is not required to balance with one foot in the air when using the device. A further advantage of the present invention is its ease of operation. The user simply pulls the strap means 36 and the sock 38 is installed on the foot 42 and pulled up the leg 44 to the proper position, at which point the installer removes itself from the sock.

Figure 6:
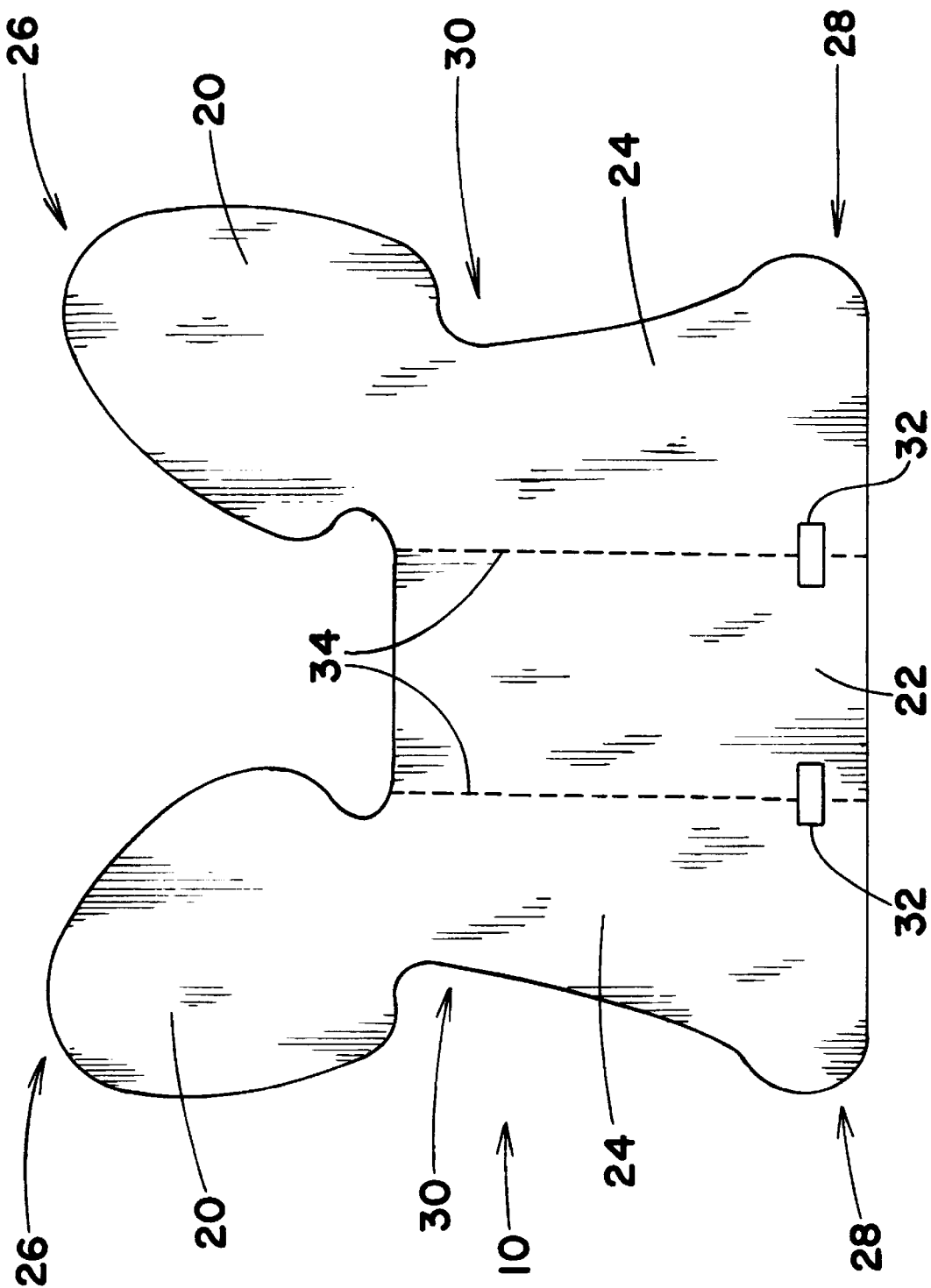
FIG. 6 is a top view of another embodiment of the flexible member of the sock and support hose installer of the present invention, as it would appear when cut from a sheet of material.

Referring to FIG. 6, an alternative embodiment of the present invention is shown. FIG. 6 is a top view of the flexible member of the sock and support hose installer, as it would appear when cut from a sheet of material. The cut flat sheet is also folded along the bend lines 34 to produce an elongated U-shaped unitary member 10 with horizontal bottom portion 22 and generally vertical side portions 24. These vertical side portions 24 have a greater height than the side portions shown in FIGS. 1 and 2. The device of FIG. 6 functions in the same fashion as the device of FIGS. 1 and 2, described above. The higher vertical sides provide a larger opening for inserting the user's foot 42 into the foot covering 38. Individuals with diabetes often have feet that are sensitive to pressure. The foot covering installer of FIG. 6 provides a means for these individuals to put on foot coverings without exerting excessive pressure on their feet or lower legs.

The invention also includes a method of using the foot covering installer, as well as a method of making the installer itself.

The method of using a manually operable device for applying foot coverings including socks, support hose and the like, comprises the steps of providing an elongated U-shaped unitary member of flexible material with horizontal bottom portion and generally vertical side portions. The U-shaped member has toe and heel ends, with the toe end side portions extending beyond the toe end bottom portion and terminating in spade shaped ends adapted to flex toward each other upon inserting the toe ends into a foot covering. The side portions each have a concave area at about a midpoint for receiving and reversibly maintaining a foot covering inserted over the toe ends. A strap means is connected to the U-shaped member heel end. The user inserts the spade shaped toe ends into an open end of the foot covering and positions a majority of the foot covering about the U-shaped member concave area. The user then inserts one foot into the U-shaped member from the heel end and draws, with the strap means attached thereto, the U-shaped member up the foot and leg of the user, and out of the open end of the foot covering, thereby positioning the foot covering on the foot and leg of the user.

The method of making a manually operable device for applying foot coverings comprises the steps of cutting from a flat, rectangular sheet of flexible material a shaped member having a spade shaped section on two adjacent corners of the rectangular sheet, a concave section on each of two opposite sides of the rectangular sheet, with each concave section adjacent a spade shaped corner section, a center cut out section between the spade shaped corner sections, and a pair of strap apertures positioned near a side of the flat member opposite the pair of spade shaped corner sections. An elongated U-shaped unitary member is formed from the shaped member, with the U shaped member having a horizontal bottom portion and generally vertical side portions and having toe and heel ends. The toe end side portions extend beyond the toe end bottom portion and terminate in spade shaped ends. The side portions each have a concave area at about a midpoint and strap apertures positioned in the heel ends. The cut flat sheet member is shaped by pressing the sheet member between form blocks. A strap means is attached to the pair of strap apertures which are positioned in the heel ends of the U-shaped unitary member.

While the invention has been particularly shown and described with reference to a preferred embodiment thereof, it will be understood by those skilled in the art that various changes in form and details may be made therein without departing from the true spirit and scope of the invention. The intent of the following claims is to cover all such changes and modifications which fall within the true spirit and scope of the invention.

I claim:

1. A manually operable device for applying foot coverings including socks, support hose and the like comprising;
   a) an elongated U-shaped unitary member of flexible material with horizontal bottom portion and generally vertical side portions, the U-shaped member having toe and heel ends, said toe end side portions extending beyond said toe end bottom portion and terminating in spade shaped ends adapted to flex toward each other upon inserting said toe ends into a foot covering, said side portions each having a concave area at about a midpoint thereof for receiving and reversibly maintaining a foot covering inserted over said toe ends; and
   b) strap means connected to said U-shaped member heel end, whereby a user inserts said spade shaped toe ends into an open end of a foot covering, positions a majority of the foot covering about said U-shaped member concave area, inserts a foot into said U-shaped member from said heel end thereof, and with said strap means attached thereto, draws the U-shaped member up the foot and leg of the user, and out of the open end of the foot covering, thereby positioning the foot covering on the foot and leg of the user.

2. The device according to claim 1 wherein the flexible material is a synthetic polymeric material.

3. The device according to claim 2 wherein said polymeric material is a thermoplastic material.

4. The device according to claim 1 wherein the flexible material is sheet aluminum metal.

5. The device according to claim 1 wherein the strap means is secured to each side of the U-shaped member heal end.

6. A method of using a manually operable device for applying foot coverings including socks, support hose and the like comprising the steps;
   a) providing an elongated U-shaped unitary member of flexible material with horizontal bottom portion and generally vertical side portions, the U-shaped member having toe and heel ends, said toe end side portions extending beyond said toe end bottom portion and terminating in spade shaped ends adapted to flex toward each other upon inserting said toe ends into a foot covering, said side portions each having a concave area at about a midpoint for receiving and reversibly maintaining a foot covering inserted over said toe ends, and strap means connected to said U-shaped member heel end;
   b) inserting said spade shaped toe ends into an open end of a foot covering, and positioning a majority of the foot covering about said U-shaped member concave area;
   c) inserting a foot into said U-shaped member from said heel end thereof; and
   d) drawing with said strap means attached thereto, the U-shaped member up the foot and leg of the user, and out of the open end of the foot covering, thereby positioning the foot covering on the foot and leg of the user.

7. A method of making a manually operable device for applying foot coverings including socks, support hose and the like comprising the steps;
   a) cutting from a flat, rectangular sheet of flexible material a shaped member having a spade shaped section on two adjacent corners of said rectangular sheet, a concave section on each of two opposite sides of said rectangular sheet, with each concave section adjacent a spade shaped corner section, a center cut out section between said spade shaped corner sections, and a pair of strap apertures positioned near a side opposite said pair of spade shaped corner sections;
   b) forming an elongated U-shaped unitary member from said shaped member, said U-shaped member having a horizontal bottom portion and generally vertical side portions, the U-shaped member having toe and heel ends, said toe end side portions extending beyond said toe end bottom portion and terminating in spade shaped ends, said side portions each having a concave area at about a midpoint, and strap apertures positioned in said heel ends, by pressing said cut flat sheet member between form blocks; and
   c) attaching a strap means to said pair of strap apertures positioned in said heel ends of said U-shaped unitary member.

* * * * *